(12) United States Patent
Aberin et al.

(10) Patent No.: US 6,406,892 B1
(45) Date of Patent: Jun. 18, 2002

(54) ACETATE-FREE PURIFICATION OF PLASMID DNA ON HYDROXYAPATITE

(75) Inventors: Cheryl S. Aberin, Rodeo; Samuel G. Franklin, El Sobrante, both of CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/866,093

(22) Filed: May 23, 2001

(51) Int. Cl.⁷ ................................................. C12P 19/34
(52) U.S. Cl. ....................................................... 435/91.1
(58) Field of Search ......................................... 435/91.1

(56) References Cited

U.S. PATENT DOCUMENTS

| | | |
|---|---|---|
| 5,707,812 A | 1/1998 | Horn et al. |
| 5,834,303 A | 11/1998 | Fujishiro |
| 5,843,731 A | 12/1998 | Yamamoto |
| 5,981,735 A | 11/1999 | Thatcher et al. |
| 6,011,148 A | 1/2000 | Bussey et al. |

FOREIGN PATENT DOCUMENTS

| | | |
|---|---|---|
| WO | WO 96/02658 | 2/1996 |
| WO | WO 96/36706 | 11/1996 |
| WO | WO 99/16869 | 4/1999 |

OTHER PUBLICATIONS

A.P. Green et al., "Preparative Purification of Supercoiled Plasmid DNA for Therapeutic Applications," *BioPharm* (1997) 10(5): 52–62.

D.M.F. Prazeres et al., "Preparative Purification of Supercoiled Plasmid DNA Using Anion–Exchange Chromatography," *Journal of Chromatography* (1998) A. 806: 31–45.

*Primary Examiner*—Terry McKelvey
(74) *Attorney, Agent, or Firm*—Townsend and Townsend and Crew LLP

(57) ABSTRACT

Plasmid DNA is purified from a cell lysate by acidifying the lysate with a combination of a mineral acid and an inorganic salt in place of the commonly used acetate buffer, allowing chromosomal DNA and other impurities to precipitate out and recovering the supernatant, and applying the supernatant directly to a hydroxyapatite chromatographic separation medium. The use of the mineral acid and organic salt avoids the degradation of the hydroxyapatite that frequently accompanies repeated use with acetate and related compounds.

7 Claims, 1 Drawing Sheet

ACETATE-FREE PURIFICATION OF PLASMID DNA ON HYDROXYAPATITE

BACKGROUND OF THE INVENTION

1. Field of the Invention

This invention resides in the field of plasmid DNA purification, and particularly the use of hydroxyapatite column chromatography to purify plasmid DNA.

2. Description of the Prior Art

Gene therapy is one of the most promising developments in the treatment of disease and genetic defects and disorders. Gene therapy is the introduction of a gene fragment into the cells of a patient, the fragment being one that when expressed provides a therapeutic benefit to the patient. One example of such a benefit is the expression of a protein that is otherwise not sufficiently expressed by the patient due to a defect in a native gene. Another is the blocking of an undesired genetic function, such as a viral infection or cancer, by introducing a mutant gene, an antisense sequence or a ribozyme.

One method of introducing genes is by the use of plasmid DNA as a vector, and the interest in gene therapy has generated a demand for highly purified plasmid DNA. The purification of plasmid DNA requires the complete removal of other cell components such as host proteins, endotoxins, chromosomal DNA and RNA. This is commonly achieved by culturing host cells, typically bacterial cells, that contain the plasmid DNA, recovering the cells by centrifugation, resuspending them in a suitable suspension buffer and performing cell lysis with an alkali lysing agent, then lowering the pH of the lysate, commonly with potassium acetate buffer at pH 5.5, to precipitate out chromosomal DNA and other cellular materials while leaving the plasmid DNA in the supernatant. The supernatant is then recovered and clarified, and plasmid DNA is isolated from the supernatant by chromatography. Suitable chromatographic techniques are anion exchange chromatography, size exclusion chromatography, and reverse phase high-performance liquid chromatography.

Hydroxyapatite is a particularly effective separation medium for proteins and nucleic acids, operating by mixed-mode ion exchange due to its inclusion of both positively and negatively charged moieties. Hydroxyapatite is thus known for its use in purifying plasmid DNA. The retention of acetate ion from the neutralization step however limits the effectiveness of hydroxyapatite, since the acetate ion tends to interact with the hydroxyapatite causing dissolution of the medium. To avoid this problem, the supernatant is commonly treated by precipitation, desalting, diafiltration or dialysis prior to chromatography. These steps, of course, are time-consuming, add to the cost of producing purified plasmid DNA, and may cause sample loss and/or denaturation.

SUMMARY OF THE INVENTION

It has now been discovered that when an alkaline cell lysate containing plasmid DNA is acidified by a mineral acid in the presence of an inorganic salt, rather than by the acetate buffer of the prior art, and the supernatant is removed from the resulting precipitate and applied directly to a hydroxyapatite chromatographic separation medium, purified plasmid DNA can be eluted from the separation medium. The intervening steps of treating the lysate according to the prior art can be eliminated with no loss of product quality. In addition to the cost and time advantage of eliminating these steps, increased product yield is anticipated. This discovery avoids the use of acetate ion and its degradative effect on hydroxyapatite. The hydroxyapatite is therefore available for reuse in a large number of purifications of further lysate supernatants. The present invention therefore resides in a method of extracting plasmid DNA from bacterial cells, in which a cell lysate is first formed by the action of an alkaline lysis agent, the lysate is then acidified with a mixture of a mineral acid and an inorganic salt, the resulting supernatant and precipitate are separated, and the supernatant is directly applied to the hydroxyapatite, the plasmid DNA then being eluted with an appropriate elution buffer. Further features of the invention and its preferred embodiments will be apparent from the description that follows.

DETAILED DESCRIPTION OF THE INVENTION AND PREFERRED EMBODIMENTS

Figure 1:
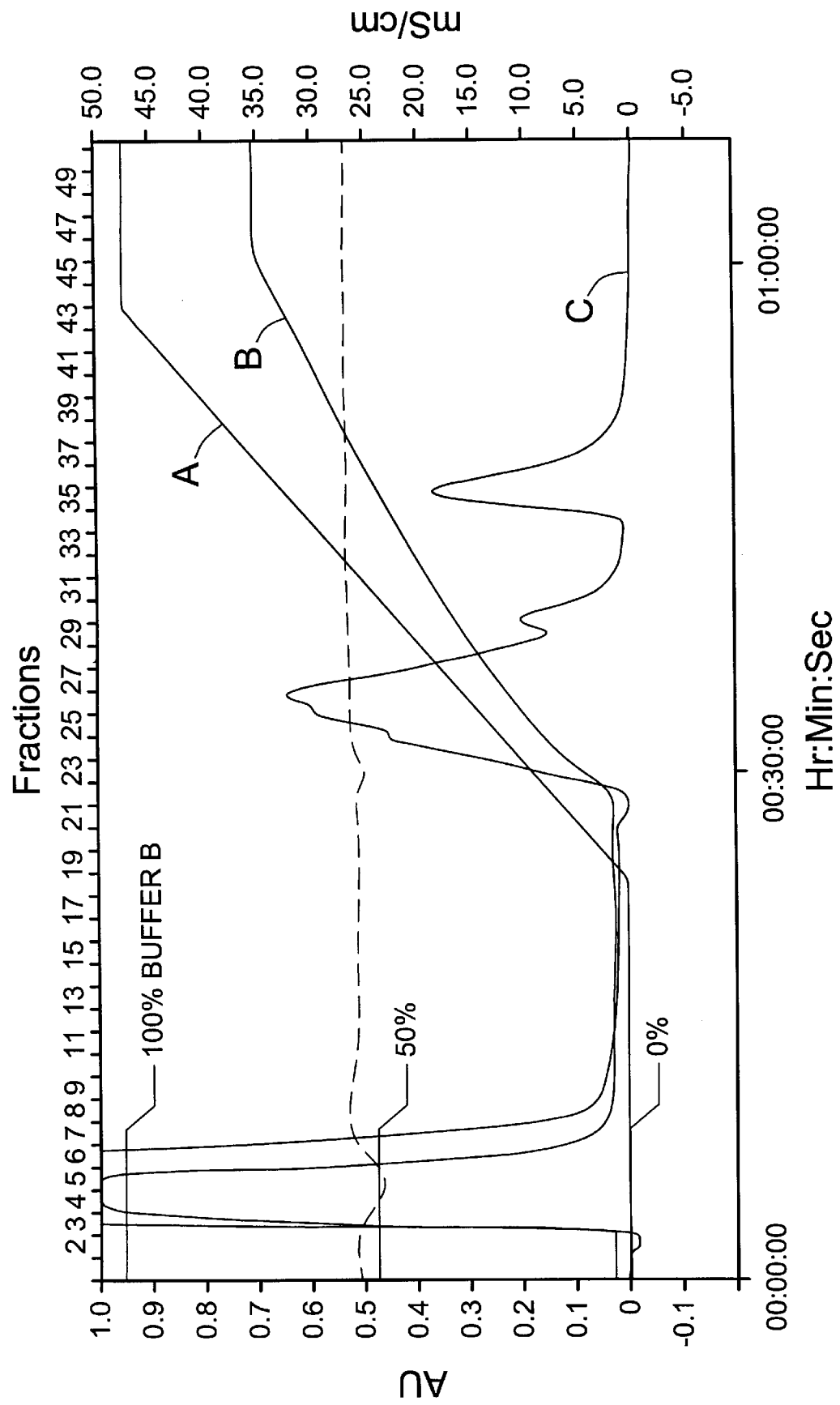
FIG. 1 is a chromatographic trace of the absorbance of an eluate from a hydroxyapatite column that had been injected with a bacterial cell lysate prepared in accordance with the present invention.

Plasmid DNA that can be purified in accordance with this invention includes any extrachromosomal DNA. The invention extends to both high copy number and low copy number plasmids, as well as runaway plasmids. The plasmids can contain selectable genes, polylinkers, origins of replication, promoters, enhancers, leader sequences, polyadenylation sites, termination sequences, and any other genetic elements that have been found to be present in plasmid structures. Plasmids encoding human genes or animal genes can be used.

The plasmid DNA can be obtained from microbial fermentations of host cells in accordance with methods well known in the art. The host cells can be any of a wide variety of microbial cells, particularly yeast cells and bacterial cells. Bacterial cells are the most commonly used for this purpose, and are therefore preferred. *E. coli* cells are particularly preferred. The fermentation process is performed in a conventional growth medium using methods well known to those skilled in the art, including batch fermentation and fed-batch fermentation. The harvesting of the host cells is likewise accomplished by conventional methods, examples of which are centrifugation, filtration, and sedimentation.

Lysis of the host cells is performed by suspending the harvested cells in an alkaline lysis medium. This step of the procedure is likewise known in the art, and is accomplished by any alkaline base that is capable of denaturing chromosomal DNA. Prominent examples are alkali metal or alkaline-earth metal hydroxides such as sodium hydroxide, potassium hydroxide, and lithium hydroxide. Dilute aqueous NaOH is commonly used. An ionic detergent is preferably present to assist in the denaturation. Sodium dodecyl sulfate is commonly used, although other suitable detergents will be readily apparent to those skilled in the art.

Once lysis has occurred, the alkaline lysate is acidified in accordance with the invention by the addition of a mineral acid and an inorganic salt. The preferred acid is hydrochloric acid. The concentration of the acid is not critical to the invention and may vary. In most cases, best results will be achieved with an acid concentration within the range of from about 0.1 N to about 1.0 N. Any inorganic salt that is highly soluble in water can be used, although preferred inorganic salts are those whose anion is the same as that of the acid. This, when hydrochloric acid is used, the preferred mineral salts are alkali metal or alkaline-earth metal chlorides, particularly sodium chloride and potassium chloride. Sufficient acid will be used to lower the pH to the acidic range, preferably to within the range of about pH 4.0 to about pH 5.0, and most preferably to within the range of about pH 4.5 to about pH 5.0. The salt concentration may vary as well, although the benefit of the salt will best be achieved with a high concentration, since the high ionic content of the resulting solution will aid in the precipitation of chromosomal DNA and other impurities and thereby separate these impurities from the plasmid DNA. In most cases, best results will be achieved with salt concentrations within the range of from about 1.0 M to about 10 M (based on a monobasic salt).

The precipitated matter resulting from the acidification step is removed by conventional means, such as centrifugation, sedimentation, or filtration, or combinations of these methods. The supernatant is then applied directly to a hydroxyapatite separation medium.

Hydroxyapatite, whose chemical formula is $Ca_{10}(PO_4)_6(OH)_2$, is a naturally occurring material which is a major constituent of bone and tooth mineral and other biological sources, and also capable of synthesis by known methods. Hydroxyapatite is widely used as a chromatographic medium or support, particularly for chromatographic separations of proteins and nucleic acids. Various hydroxyapatite chromatographic media are available commercially, and any available form of the material can be used in the practice of this invention. Preferred hydroxyapatites for use in this invention are those that are agglomerated to form particles and sintered at high temperatures into a stable porous ceramic mass. The particle size is not critical and may vary widely, but a typical particle size ranges from about 1 μm to about 1,000 μm in diameter, preferably from about 10 μm to about 100 μm. The porosity may also vary widely. In most cases, best results will be achieved with an average pore diameter of from about 100 Å to about 10,000 Å, or preferably from about 500 Å to about 3,000 Å. An example of a ceramic hydroxyapatite material that will serve effectively in the practice of this invention is MACRO-PREP® Ceramic Hydroxyapatite, Types I and II, a product of Bio-Rad Laboratories, Inc., Hercules, Calif., USA.

The isolation of plasmid DNA by hydroxyapatite can be achieved by a packed hydroxyapatite column or any of the other configurations that are used or known for use in chromatographic separations. Elution of the plasmid DNA from the hydroxyapatite is typically achieved by an elution buffer of conventional composition, with such common modifications as a salt gradient to help separate the plasmid DNA from other components remaining in the clarified supernatant of the acidified lysate.

The following example is offered for illustrative purposes only.

EXAMPLE

This example illustrates the purification of DNA of A plasmid derived from pUC 19 on a hydroxyapatite column in accordance with the present invention. This plasmid has an optical density reading of 350 optical density units per 100 mL of cell culture at a wavelength of 260 nm.

The plasmid was grown in E. coli. in Terrific Broth, supplemented with 100 μg/mL ampicillin according to conventional methods. For use as a control, a 25-mL aliquot of the culture was purified with a Plasmid Midiprep kit (Bio-Rad Laboratories, Inc., Hercules, Calif., USA). For the test, another 25-mL aliquot of the culture was lysed by resuspending the cells in 40 mM sodium phosphate, pH 8.0 and 25 mM ethylene diamine tetraacetic acid (EDTA) on an ice bath. A cell lysis solution consisting of 1% sodium dodecyl sulfide and 0.2 N NaOH was then added to the suspension, mixed immediately, and stored on ice for 3–5 minutes. One mL of 3 M KCl was added immediately and mixed, and the resulting suspension was adjusted to pH 4.5 with 1.0 N HCl, then neutralized to pH 7.0 with aqueous NaOH. The crude lysate was centrifuged at 15,000 g for 20 minutes at 4° C. The precipitates were removed by filtering on a 70-μm nylon cell strainer.

A 5-mL aliquot of the plasmid-containing lysate (892μg/mL) was then injected onto a ceramic hydroxyapatite column (ECONO-PAC CHT II cartridge from Bio-Rad Laboratories, Inc., with average particle size 20 μm±10, nominal pore diameter 800–1,000Å, cartridge volume 5 mL). The column was washed with five volumes of 10 mM sodium phosphate plus 1 mM EDTA, pH 7.0, followed by a linear gradient in which the OF PLASMID DNA ON HYDROXYAPATITE sodium phosphate concentration was raised to 0.4 M over ten column volumes at 1.5 mL/min flow rate.

The elution was monitored at 254 nm and fractions were collected and analyzed spectrophotometrically at 260 nm for DNA content and at 280 nm for protein content. FIG. 1 is a trace of the chromatogram showing the imposed conductivity (line A, reflecting the sodium phosphate gradient), the measured conductivity (line B), and the absorbance (line C, shown in absorbance units as a fraction of the full scale). The numbered fractions are shown along the top of the trace and the elapsed time along the bottom. The purity of the plasmid was then determined by electrophoresis on a 0.8% agarose gel. Comparison of this chromatogram with a corresponding chromatogram performed on the control sample indicated that the peak spanning fractions 35–37 was the pure plasmid DNA.

These three fractions and the control were analyzed by electrophoresis in separate lanes on a single 0.8% agarose gel, which confirmed that the fractions were the pure plasmid DNA.

Separately, fractions 35–37 were digested with EcoR I restriction enzymes, and both the undigested and digested forms were analyzed by electrophoresis on a 0.8% agarose gel. Examination of the gel indicated that the supercoiled DNA (undigested) migrated faster than the linearized (digested) DNA, confirming that fractions 35–37 contained the plasmid DNA.

The foregoing descriptions are offered for purposes of illustration. Modifications and substitutions of the various materials, reagents, operating conditions, and procedural steps, which also fall within the scope of the invention, will be apparent to those skilled in the art upon reading these descriptions.

What is claimed is:

1. A method of extracting plasmid DNA from biological cells, said method comprising:
   (a) contacting said cells with an alkaline lysing agent to form a cell lysate;
   (b) acidifying said cell lysate to a pH of from about 4.0 to about 5.0 with a mineral acid in the presence of an inorganic salt to cause formation of a precipitate and a supernatant;

(c) separating said supernatant from said precipitate and neutralizing said supernatant to a pH of from about 7.0 to about 7.5; and (d) directly applying said neutralized supernatant to a hydroxyapatite chromatographic medium, and eluting purified plasmid DNA from said medium.

2. A method in accordance with claim 1 in which step (b) comprises acidifying said cell lysate with hydrochloric acid in the presence of a member selected from the group consisting of alkali metal and alkaline-earth metal chlorides.

3. A method in accordance with claim 1 in which step (b) comprises acidifying said cell lysate with hydrochloric acid in the presence of a member selected from the group consisting of sodium chloride and potassium chloride.

4. A method in accordance with claim 1 in which step (b) comprises acidifying said cell lysate with hydrochloric acid in the presence of potassium chloride.

5. A method in accordance with claim 1 in which step (b) comprises acidifying said cell lysate to a pH of from about 4.5 to 5.0 with hydrochloric acid in the presence of a member selected from the group consisting of alkali and alkaline earth metal chlorides.

6. A method in accordance with claim 1 in which said hydroxyapatite chromatographic medium is sintered hydroxyapatite.

7. A method in accordance with claim 1 in which step (d) comprises eluting said purified plasmid DNA with a salt gradient.

* * * * *